US007606722B2

(12) United States Patent
Kalies

(10) Patent No.: US 7,606,722 B2
(45) Date of Patent: Oct. 20, 2009

(54) METHOD FOR ASSIMILATING AND USING PHARMACY DATA

(75) Inventor: Ralph F. Kalies, Pickett, WI (US)

(73) Assignee: Omnicare, Inc., Covington, KY (US)

( * ) Notice: Subject to any disclaimer, the term of this patent is extended or adjusted under 35 U.S.C. 154(b) by 501 days.

(21) Appl. No.: 10/682,157

(22) Filed: Oct. 8, 2003
(Under 37 CFR 1.47)

(65) Prior Publication Data
US 2004/0148196 A1 Jul. 29, 2004

Related U.S. Application Data

(60) Provisional application No. 60/416,798, filed on Oct. 8, 2002.

(51) Int. Cl.
G06Q 10/00 (2006.01)
G06Q 50/00 (2006.01)
A61B 5/00 (2006.01)
G06F 19/00 (2006.01)

(52) U.S. Cl. .................. 705/2; 705/3; 705/16; 705/22; 705/26; 705/27

(58) Field of Classification Search ............... 705/1, 705/2, 3, 4
See application file for complete search history.

(56) References Cited

U.S. PATENT DOCUMENTS

| 5,706,441 A * | 1/1998 | Lockwood ............... 705/3 |
| 5,737,539 A * | 4/1998 | Edelson et al. .......... 705/3 |
| 5,781,893 A * | 7/1998 | Felthauser et al. ...... 705/10 |
| 5,845,255 A | 12/1998 | Mayaud ................... 705/3 |
| 5,924,073 A * | 7/1999 | Tyuluman et al. ........ 705/2 |
| 5,946,659 A * | 8/1999 | Lancelot et al. ......... 705/3 |
| 5,956,689 A * | 9/1999 | Everhart, III ........... 705/3 |
| 6,014,631 A * | 1/2000 | Teagarden et al. ...... 705/3 |
| 6,061,657 A * | 5/2000 | Whiting-O'Keefe ..... 705/2 |
| 6,064,968 A * | 5/2000 | Schanz ................... 705/1 |
| 6,195,612 B1 * | 2/2001 | Pack-Harris ............ 702/2 |
| 6,356,873 B1 | 3/2002 | Teagarden et al. ...... 705/3 |
| 6,430,539 B1 | 8/2002 | Lazarus et al. ......... 705/10 |
| 6,430,545 B1 | 8/2002 | Honarvar et al. ....... 706/47 |
| 6,694,334 B2 | 2/2004 | DuLong et al. |
| 6,697,783 B1 | 2/2004 | Brinkman et al. |
| 2001/0037216 A1 | 11/2001 | Oscar et al. ............ 705/2 |
| 2002/0032582 A1 | 3/2002 | Feeney, Jr. et al. ..... 705/2 |
| 2002/0042723 A1 | 4/2002 | Rice et al. .............. 705/2 |
| 2002/0042725 A1 | 4/2002 | Mayaud ................. 705/2 |
| 2002/0087967 A1 | 7/2002 | Conkwright et al. ... 725/1 |
| 2002/0133379 A1 | 9/2002 | Lewis et al. ............ 705/4 |
| 2002/0143579 A1 | 10/2002 | Docherty et al. ....... 705/2 |
| 2002/0169727 A1 | 11/2002 | Melnick et al. ...... 705/400 |
| 2003/0093295 A1 * | 5/2003 | Lilly et al. .............. 705/2 |

* cited by examiner

Primary Examiner—Gerald J. O'Connor
Assistant Examiner—Amber L Altschul
(74) Attorney, Agent, or Firm—Ostrolenk Faber LLP

(57) ABSTRACT

A method for assimilating and using pharmacy data to determine actual consumption of medications from particular sources, such as pharmaceutical companies. Transaction records are accumulated and correlated, and medication dispensing and usage data is extracted to determine actual consumption information. In an alternate embodiment, the transaction records and dispensing data are examined for identifiable usage patterns. The patterns form the basis for a set of rules that can then be used to calculate actual consumption data from transaction records.

12 Claims, 3 Drawing Sheets

US 7,606,722 B2

METHOD FOR ASSIMILATING AND USING PHARMACY DATA

This application claims the benefit of U.S. Provisional Patent Application No. 60/416,798, filed Oct. 8, 2002, the contents of which are hereby incorporated by reference.

FIELD OF THE INVENTION

This invention relates to a method for managing pharmacy data. Specifically, the invention relates to a method for assimilating large quantities of pharmacy transactions and extracting relevant data relating to a particular type of medication.

BACKGROUND OF THE INVENTION

The practice of dispensing medication via a pharmacy has undergone radical change in recent years, with a paradigm shift from small, independent pharmacies to regional and national networks of Publicly-held Corporate Pharmacies ("PCPs"). The advent of PCPs was in response to a desire by the industry to minimize the cost of drug therapy while maximizing profitability. Under the PCP system, much of the decision-making power is shifted from health care providers to an administrative organization that establishes standards of care, standardizes methods of delivering care, and evaluates the outcomes of given care. PCPs work to minimize costs and maintain profits through a variety of means, including volume purchases, quality control, formulary lists of preferred medications, discounts for movement of market share, and negotiated healthcare fees.

Since PCPs focus on reducing the cost of health care and maintaining profits, there is a high degree of interest in acquiring as much historical and timely ongoing data as possible regarding medication use and benefit, comparative costs of alternate therapies, and patient demographics. This information can be collected, organized and stored in a database or "data warehouse" for use in a wide variety of medical and economic analyses. A data warehouse is a process by which large quantities of related data from many operational systems is merged into a single standard repository to provide an integrated information view based on logical queries. Types of logical queries may relate to "data mining," which can be defined as a process of data selection, exploration and building models using vast data stores to discover previously unknown relationships and patterns. Other queries may be in support of clinical research on a particular medication or malady.

PCPs regularly conduct a number of data reviews as part of the quality control process. In general, these reviews include a Drug Utilization Review ("DUR") and a Drug Usage Evaluation ("DUE"). These reviews seek to establish best practices for maximizing patient benefit, optimizing PCP expenditures, and maintaining profitability by minimizing the number of different medications used for the same treatments and optimizing market share for the medicines used.

As part of the cost-containment process, a PCP typically negotiates price discounts and other incentives with its source of prescription medications, the pharmaceutical companies. These discounts are often based on the volume of the companies' products used by the PCP and gains in the pharmaceutical companies' market share that are attributable to the PCP. This creates a need for the PCP to obtain accurate actual consumption data for the medications dispensed by its network of pharmacies. Unfortunately, this data is not always readily available. This is due in part to the fact that a particular prescription may be partially fulfilled in several "transactions." A transaction typically includes such information as patient name, prescribing physician, medication name, prescription quantity, quantity dispensed, pharmacist's name, and date of fulfillment. A transaction may also include usage information, such as one or more returns of part or all of a prescription. In addition, the prescription may be fulfilled with generics or medications from several companies in separate transactions. These variables make it difficult to track actual consumption of a particular company's product for a given prescription. When computing actual medication consumption, the errors introduced by summing individual transaction records are magnified when large numbers of transactions are involved, creating an unacceptable margin of error. Further, manual extraction of dispensing and usage data is both time-consuming and labor-intensive. There is a need for a timely method that can assimilate prescription data longitudinally from pharmacy transaction data such that the prescription data can be more accurately accumulated and analyzed to aid the PCP decision-making and cost negotiation processes.

SUMMARY OF THE INVENTION

According to the present invention, a method is disclosed for efficiently and accurately computing medication dispensing and usage data and making the information available for a variety of medical and economic analyses, including determining the amount of medications actually consumed by the members participating in a PCP. Transaction records are correlated and matched for a particular patient prescription to obtain an accurate account of the brands and quantities of medications used to fulfill the prescription. In one embodiment of the present invention, correlated dispensing and return data for pharmacy transaction records are examined compute actual consumption data for selected medications supplied by selected sources. In an alternate embodiment of the present invention, transaction records from several participating pharmacies within a PCP are obtained as a representative example. Dispensing and usage data is extracted from the records provided by each pharmacy, then consolidated into a single report. The report is then examined for dispensing and usage patterns. Any exceptions to the patterns are also noted, along with the reasoning for the exceptions. The patterns and exceptions are reviewed with the sources of the data to ensure a full understanding of the underlying causes for the patterns and exceptions. The patterns and exceptions are then used to form logical rules and assumptions regarding the dispensing and usage of medications within the sending pharmacies. The rules and assumptions are tested using a batch of transaction data from PCP pharmacies and then reviewed for accuracy. If the test does not produce results with acceptable accuracy, the patterns in the consolidated report are re-examined for any hidden patterns or exceptions, or the previous mis-interpretation of recorded patterns and exceptions. Once acceptable results are achieved, the rules may be applied to all of the pharmacies' prescription transaction data in order to measure the actual consumption of selected medications and supplies during any given period of time without a need to continually correlate transactions to prescriptions in order to derive dispensing and usage data.

BRIEF DESCRIPTION OF THE DRAWINGS

Further features of the present invention will become apparent to those skilled in the art to which the present invention relates from reading the following specification and claims with reference to the accompanying drawings, in which:

DESCRIPTION OF THE PREFERRED EMBODIMENT(S)

In the discussion that follows it should be noted that structural components of the present invention are identified with numerals, while steps, tasks or actions are identified with numerals having a prefix "s." In addition, the same numerals are used in the various embodiments described below where the numerals refer to the same components and/or steps.

Figure 1:
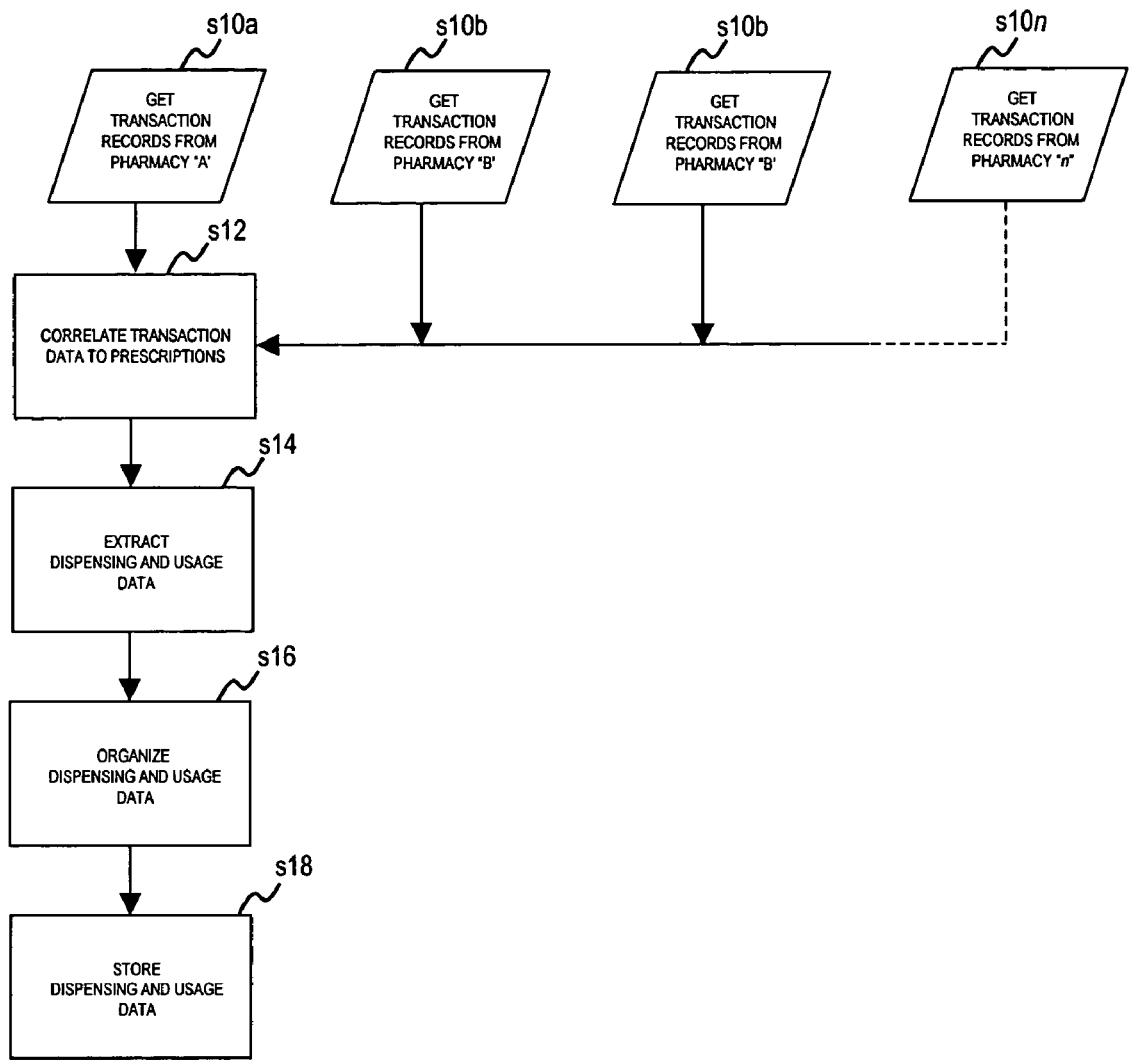
FIG. 1 is a flow diagram of a method for assimilating medication dispensing and usage data according to an embodiment of the present invention.

A flow diagram showing an overview of a method for assimilating medication dispensing and usage data according to an embodiment of the present invention is shown in FIG. 1. In steps s10a-c, transaction records relating to prescriptions are gathered from at least one participating pharmacy within a PCP, such as Pharmacy "A," Pharmacy "B" and Pharmacy "C." Three pharmacies are depicted in FIG. 1 for the purpose of illustration, but a greater or fewer number may be involved. The transaction records are correlated to prescriptions at step s12 to match up at least one transaction record to a particular prescription. In many cases more than one transaction record will be associated with a particular prescription, representing such transaction types as partial fulfillment of the prescription and returns of unused medication. At step s14 the dispensing data for the prescriptions is extracted from the correlated transaction records. Dispensing data may include medication description, NDC number, a transaction identification number, date filled, patient information, payment and insurance plans, quantities dispensed, returns of unused medication, manufacturers and other sources for the medication, payment amounts, usual and customary charges, co-pay amount, ingredient costs, and fees. Usage data may also be obtained during step s14. Usage data may include the total amount of medication for a selected prescription that has been returned, discarded or is otherwise not consumed. At step s16 the dispensing and usage data obtained at step s14 is organized to permit later logical queries, such as determining the sources of the medications used to fulfill the prescription, particularly selected brand names and selected pharmaceutical companies.

The data organized at s16 is stored at step s18 for later use. Any of the transaction records, dispensing data and usage data may be stored separately or in combination at a data repository 204, discussed below. Further, the transaction records, dispensing data and usage data may be communicated to data repository 204 via an electronic communications network and protected from unauthorized access by any one of a number of conventional means. The data repository, electronic communications network and access control are discussed in more detail below.

Figure 2:
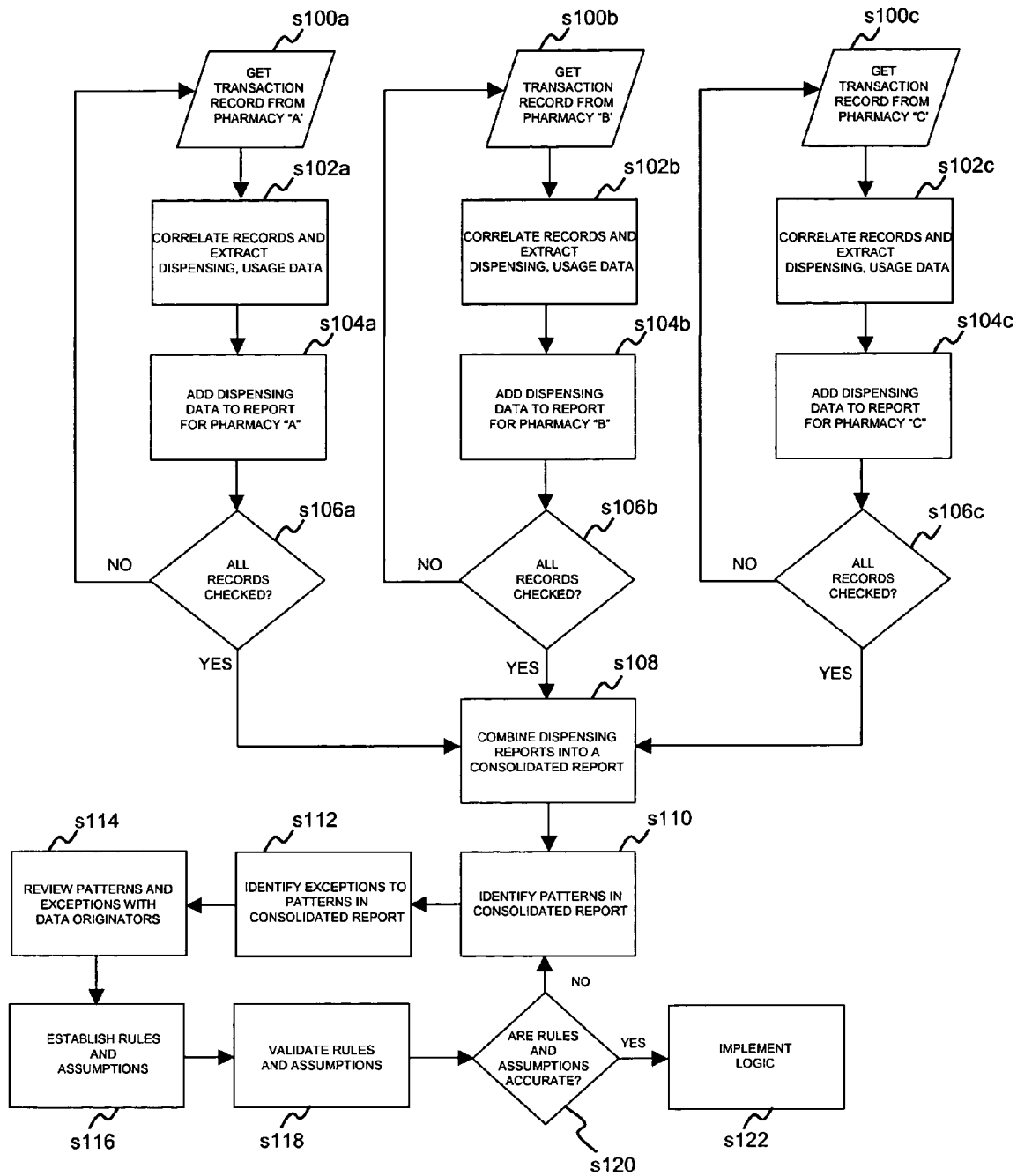
FIG. 2 is a flow diagram of a method for establishing a set of rules and assumptions for calculating medication dispensing and usage data according to an embodiment of the present invention.

FIG. 2 depicts a method for establishing a set of rules and assumptions for calculating medication dispensing and usage data according to one embodiment of the present invention. At step s100a-c, prescription transaction records are gathered from a representative number of participating pharmacies within a PCP, such as Pharmacy "A," Pharmacy "B," and Pharmacy "C." Three pharmacies are depicted in FIG. 2 for the purpose of illustration, but a greater or fewer number may be used. Transaction records are correlated to prescriptions, and dispensing and usage data is extracted from the transactions at step s102a-c in the manner previously described for steps s12 and s14 of FIG. 1. The dispensing and usage data is accumulated into a summary report at step s104a-c. The summary report may provide such information as the number of transactions for each prescription, the quantity of medicine dispensed, discarded or returned in each transaction, and the total quantity of medicine dispensed and/or returned. The process of extracting and accumulating data at steps s100a-c through s104a-c continues until all records have been checked at step s106a-c. At step s108, the summary reports from step s104a-c are consolidated into a single report containing representative medicine dispensing and usage data for the PCP Pharmacies A-C. The consolidated report of step s108 is then examined for dispensing and usage patterns at step s110. Example dispensing and usage metrics include, but are not limited to, the ratio of medication dispensed and returned for specific prescriptions, the number of transactions per prescription, dispensing habits of individual physicians, prescription data to patient demographics, and prescription habits for particular medications for individuals or classes of patients and/or prescribing physicians. Any significant exceptions to the patterns of step s110 are also noted at step s112. Example exceptions may include medications normally used to treat a particular ailment or disease but contraindicated for such reasons as interactions with other medications, or patient or disease sensitivities. The patterns and exceptions of steps s110 and s112 are then reviewed with the originators of the data (i.e., Pharmacies A-C) at step s114 to ensure that the patterns and exceptions are valid, that the reasons for the patterns and exceptions are understood, and that the patterns and exceptions are generally applicable rather than anomalous. A set of logical rules and assumptions are then established at step s116 using the patterns and exceptions as a basis. The nature of the rules and assumptions is that various characteristics, data points and key indicators of a given dataset may be examined to calculate the quantity of medications actually consumed by customers of the PCP participating pharmacies (i.e., the amount dispensed less the amount unused) without resorting to a review of each individual prescription and each transaction.

The rules and assumptions are first validated at step s118 to ensure that the calculated "actual-consumption" data values are sufficiently representative of the amount of medication consumed. One way to validate the rules and assumptions is to first, identify a reasonably representative set of pharmacy data from a PCP participating pharmacy other than Pharmacies A-C; next, calculate actual consumption using rules and assumptions; then, compute the actual consumption by reviewing each transaction in the dataset; then, compare the calculated consumption to the computed consumption. The results are preferably verified at a number of levels, including patient, nursing facility and PCP levels of medicine consumption. If the accuracy of the results at step s120 are outside a predetermined margin of error, the data of step s108 can be re-examined beginning at step s110. If adequate accuracy cannot be achieved, data from a greater number of pharmacies may be used to generate a new consolidated report at s108 for considering a revision of the rules and assumptions.

Alternatively, a larger set of pharmacy transaction data may be required for step s100a-c. It may be preferable to generate a new consolidated report for review using both a larger dataset and data from a greater number of pharmacies. If the accuracy of the test results at step s120 are acceptable, the rules and assumptions may be applied to all of the prescription transaction data within the PCP network, as depicted by step s122. The tested logic of step s122, comprising rules and assumptions about the transaction records, may be applied to future transaction records to obtain estimates, or "calculations" of dispensing and return data without a need to continuously extract dispensing and usage data from individual transaction records. The process of FIG. 2 is preferably repeated periodically to ensure continued accuracy of the logic derived at step s122 and identify any trends that might affect the accuracy rules and algorithms and, in turn, the derived data.

Figure 3:
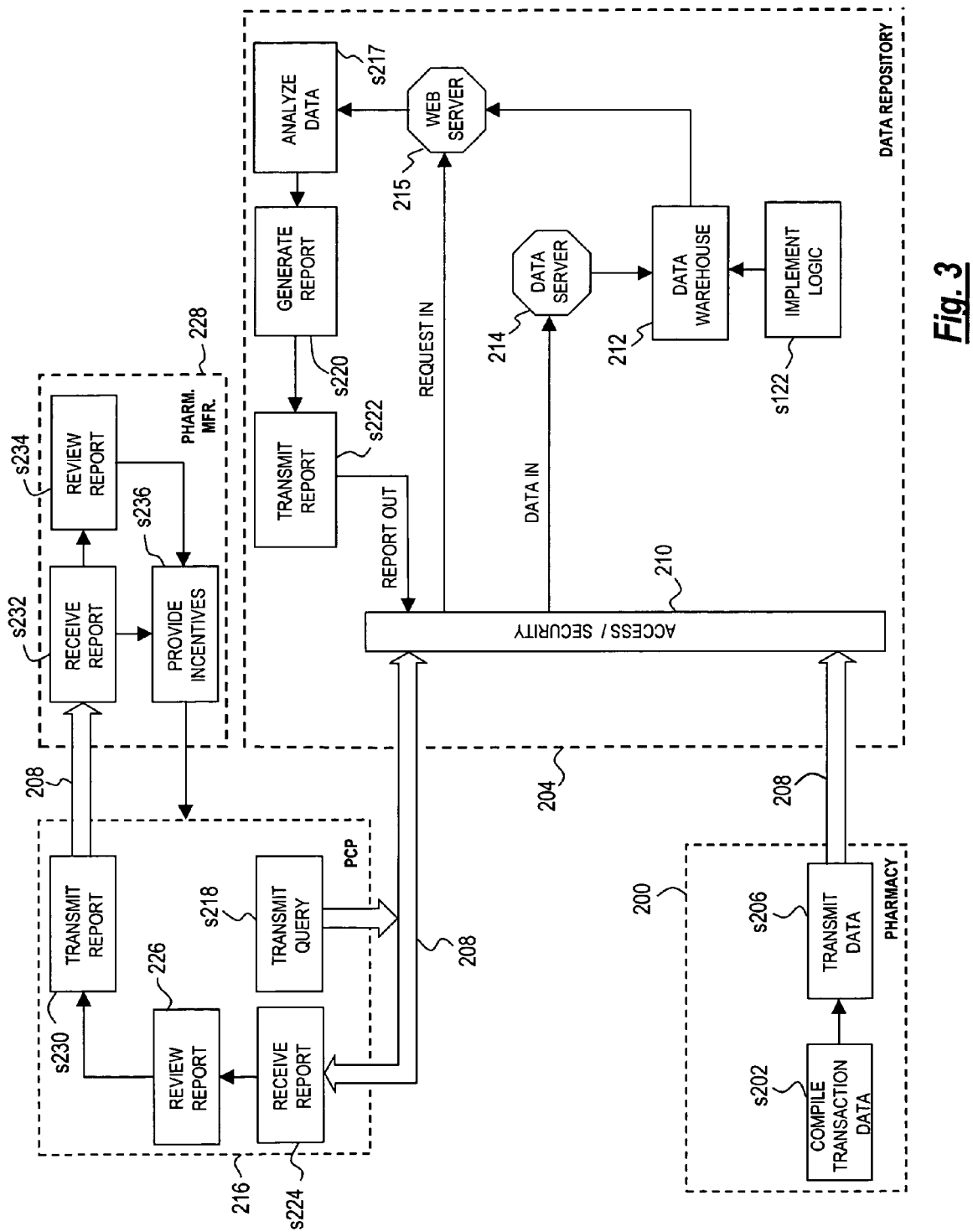
FIG. 3 is a flow diagram of a method for assimilating, storing and using medication dispensing and usage data according to an embodiment of the present invention.

A block diagram of a method for utilizing the assimilated prescription data according to an embodiment of the present invention is shown in FIG. 3. At least one pharmacy 200 compiles prescription transaction data, as at s202, in the normal course of its business. The data may be packaged into a compilation such as a computer file, such as a batch file compatible with a conventional file transfer protocol ("FTP"). The batch file is communicated to a data repository 204 on a regular basis, as at s206. The compiled data may be communicated by any convenient means, such as an electronic communications network 208. Electronic communications network 208 may take any convenient form, such as computer networks, facsimile, intranets, the Internet, teletype, telephony, switches, high-speed lines and frame relays. Electronic communications network 208 may optionally include one or more conventional means of protecting the pharmacy data in order to ensure patient privacy and to prevent data tampering and alteration. Protection means include, but are not limited to, encryption, firewalls and virtual private networks ("VPNs"). When the compiled data is received at data repository 204, it may be subjected to an access/security screen at s210. The access/security screen s210 may include verification of the data source, a validity check of the file and/or data, and a check for computer viruses. If the data is deemed acceptable, it is forwarded to a data warehouse 212 by a data server 214.

Data server 214 is a conventional computer server system, such as a file server, disk server, or database server. Data server 214 is adapted such that it is in electronic communication with access/security screen function s210 to receive accepted data. Data server 214 is in further electronic communication with data warehouse 212 such that the data server can forward accepted data to the data warehouse for storage and later analysis.

After the transaction data has been accumulated in the data warehouse 212, a requestor such as a PCP 216 may make logical queries of the stored data. A query is a structured method of retrieving relevant information from accumulated data stored in a data warehouse. An example query would be to determine usage data for a selected medication supplied by a selected company over a specified period of time.

With reference to FIG. 3, as part of its ongoing business operations, a Publicly-held Corporate Pharmacy (PCP) 216 may identify a market for selected medications and a selected source for the medications, such as a pharmaceutical company 228. The PCP 216 and pharmaceutical company 238 may enter into an agreement whereby the pharmaceutical company will provide the PCP with discounts or incentives in exchange for the PCP's successful efforts to increase the pharmaceutical company's share of the identified market. To obtain evidence of such market share gains, PCP 216 may transmit a query for actual consumption data to data repository 204 via electronic communications network 208, as at s218. The query must first pass the access/security screen s210 to ensure that the source of the query is permitted access to the data warehouse 212. The portion of access/security screen s210 pertaining to restricting access to the data stored within data repository 204 may be accomplished by any conventional means, such as predetermined usernames, passwords, and secured websites. The level of security may be enhanced by conventional "anti-hacking" methodologies, such as encrypted passwords, case-sensitive passwords, passwords requiring pseudorandom combinations of numbers and letters, and limiting the number of access attempts. An accepted query is passed to data warehouse 212 via a web server 215.

Web server 215 is a conventional computer server system, such as a file server, disk server, or database server. Web server 215 is adapted such that it is in electronic communication with access/security screen 210 to receive accepted queries. Web server 215 is in further electronic communication with data warehouse 212 such that the web server can forward the data pertaining to the query to a report generation function s220.

In an embodiment of the present invention, medication dispensing and usage data stored in data warehouse 212 may be utilized to directly compute actual consumption data pertaining to one or more selected medication provided by one or more selected sources, such as a pharmaceutical company. "Actual consumption" may be defined as the total amount of a selected medication that is actually consumed, taking into account the total amount of the medication dispensed less the total amount that is returned or is otherwise not used. In this embodiment, termed the "Computation Method," an analysis step s217 may obtain a predetermined set of transaction data from data warehouse 212 via web server 215. Each transaction record is then analyzed to determine the total amount of medicine actually consumed for a selected medication, such as a brand of medication, taking into account such factors as the total amount of medicine dispensed and the total amount of unused medicine returned or otherwise unused. The actual consumption data of each transaction in the dataset may then be summed to derive a total actual consumption value. Using logical queries, actual consumption data for the dataset may be determined for at least one selected medication supplied by at least one selected source.

In an alternate embodiment of the present invention, termed the "Calculation Method," the pharmacy transaction data is analyzed at step s217 using the logical rules and assumptions of FIG. 2 to calculate actual consumption data pertaining to one or more selected medication provided by one or more selected sources, such as a pharmaceutical company. The rules and algorithms of s122 may be applied to any predetermined set of pharmacy data. Using the rules and algorithms of s122 in conjunction with predetermined characteristics, data points and key indicators of the dataset, analysis step s217 examines the data to calculate the actual consumption data without resorting to a review of each individual prescription and each transaction.

Although the Computation Method is less efficient, more resource-intensive and more time-consuming in comparison to the Calculation Method, actual consumption data determined in this manner is highly accurate. In some embodiments of the present invention Calculation Method may be used in conjunction with the Computation Method. In such embodiments the Calculation Method is used on a regular basis to efficiently and quickly calculate actual consumption data, with the Computation Method being performed periodically as a cross-check to validate the previously calculated values. Calculated values falling within a predetermined statistical tolerance range may be deemed acceptable, whereas values falling outside a tolerance range may provide an indication that a review and potential revision of the rules and assumptions may be needed.

A report summarizing the actual consumption data is generated at s220 and is communicated to the PCP at s222 via access/security screen s2110 and electronic communications network 208. PCP 216 receives and reviews the report at s224, s226 respectively, then communicates the report to the selected pharmaceutical company 228 as shown at s230. The report may be communicated via electronic communications network 208, if desired. The selected pharmaceutical company 228 receives and reviews the report at s232, s234 respectively and then provides PCP 216 with incentives such as volume discounts, as at s236. The terms of the incentives may optionally be in a predetermined proportion to the amount of market share gain for the pharmaceutical company accomplished by the PCP. Types of incentives include, but are not limited to, discounts on future purchases and rebates on present purchases.

With continued reference to FIG. 3, in an optional embodiment of the present invention the pharmacy data may be encrypted prior to transmission by participating pharmacy 200 in order to protect patient privacy and maintain the integrity of the transmitted data. In this embodiment of the present invention, encrypted data accepted by access/security screen 210 is decrypted to restore the data to a usable form prior to storing it. Any conventional computer data encryption/decryption method may be used, such as asymmetric key-based algorithms wherein one electronic code or "key" is used to encrypt data and a different key is used to decrypt the same data. Symmetric key-based algorithms, or block-and-stream ciphers may also be used. Using these cipher types, the data are separated into portions, and those portions are encrypted and decrypted based on a specific key. Stream ciphers may also be used, wherein the portions are encrypted on a bit-by-bit basis. Likewise, reports communicated from data repository 204 to a requestor, such as PCP 216, may optionally be encrypted in any conventional manner before the report is transmitted from the data repository. The requester, such as 216 then decrypts the report in any conventional manner after receiving it. Similarly, reports from PCP 216 to a pharmaceutical company 228 may be encrypted before transmission and then decrypted after reception.

While this invention has been shown and described with respect to several detailed embodiments thereof, it will be understood by those skilled in the art that various changes in form and detail thereof may be made without departing from the scope of the claims of the invention. One skilled in the art will recognize that many of the separately-described functions of the various embodiments of the present invention may be combined, rearranged or eliminated to accomplish the desired result without affecting the scope of the invention. The embodiments disclosed herein are for illustrative purposes only and are not intended to be limiting with regard to the arrangement or combination of the components of the present invention.

What is claimed is:

1. A method of a processor determining consumption of medication dispensed pursuant to a prescription for medication at one or more pharmacies, the method comprising the steps of:
   a) the processor obtaining over a communication network a plurality of electronic medication dispensation transaction records from the one or more pharmacies in response to a request for the transaction records;
   b) the processor correlating the obtained medication dispensation transaction records to the prescription;
   c) the processor extracting medication dispensing data and medication usage data from the correlated medication dispensation transaction records, wherein the medication usage data includes an amount of medication in the prescription that has been returned or not consumed;
   d) the processor consolidating medication dispensing data and medication usage data related to the same prescription dispensed at all of the one or more pharmacies;
   e) the processor identifying at least one pattern in the medication dispensing data and medication usage data;
   f) the processor formulating at least one logical rule from the pattern for calculating medication actual consumption data;
   g) the processor testing the at least one logical rule for accuracy on at least one subsequent transaction record; and
   h) the processor calculating medication actual consumption data pursuant to the at least one logical rule comprising:
      i) at least one of a plurality of sources for the medications dispensed, wherein the plurality of sources include a plurality of pharmaceutical companies; and
      ii) at least a portion of the actual consumption of the medication that is respectively attributable to at least one of the plurality of sources.

2. A method according to claim 1, further comprising the steps of
   a) compiling the transaction records;
   b) communicating the transaction records to a data repository; and
   c) storing the transaction records in a data warehouse of the data repository.

3. A method according to claim 2, further comprising the steps of:
   a) receiving a query for actual consumption data from a requestor;
   b) generating a report responsive to the query; and
   c) communicating the report to the requestor.

4. A method according to claim 3, wherein the query and the report are communicated via an electronic communications network.

5. A method according to claim 4, wherein the report is encrypted by the data repository before communicating it to the requestor, and wherein the requestor decrypts the report after receiving it.

6. A method according to claim 4, further comprising the step of adding security measures to prevent unauthorized access to the query and report.

7. A method according to claim 2, wherein the transaction records are communicated via an electronic communications network.

8. A method according to claim 7, wherein the electronic communications network is an intranet.

9. A method according to claim 7, further comprising the step of adding security measures to prevent unauthorized access to the transaction records.

10. A method according to claim 1, further comprising the steps of:
 a) identifying at least one market for at least one selected medication, for at least one selected source of the plurality of sources;
 b) periodically calculating actual consumption data for the selected medication;
 c) periodically communicating actual consumption data to the selected source; and
 d) computing an incentive to be received from the selected source, the value of which correlates to a change in market share for the selected medication in favor of the selected source, as shown by the calculated actual consumption data.

11. A method according to claim 10, wherein the actual consumption data is communicated to the source via an electronic communications network.

12. A method according to claim 1, wherein the step of identifying at least one pattern in the medication dispensing data and medication usage data further includes identifying exceptions to the pattern.

* * * * *

UNITED STATES PATENT AND TRADEMARK OFFICE
CERTIFICATE OF CORRECTION

PATENT NO. : 7,606,722 B2 Page 1 of 1
APPLICATION NO. : 10/682157
DATED : October 20, 2009
INVENTOR(S) : Ralph F. Kalies It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 907 days.

Signed and Sealed this

Twelfth Day of October, 2010

David J. Kappos
*Director of the United States Patent and Trademark Office*